United States Patent [19]

Bryan

[11] Patent Number: 4,957,441

[45] Date of Patent: Sep. 18, 1990

[54] METHOD OF ENHANCING THE CURING OF A PHOTOCURABLE DENTAL RESTORATIVE MATERIAL

[75] Inventor: Thomas T. Bryan, Mahtomedi, Minn.

[73] Assignee: Minnesota Mining and Manufacturing Company, St. Paul, Minn.

[21] Appl. No.: 287,003

[22] Filed: Dec. 20, 1988

[51] Int. Cl.⁵ .............................................. A61K 5/01
[52] U.S. Cl. .................................. 433/228.1; 433/226
[58] Field of Search ............... 433/226, 227, 228, 215, 433/229

[56] References Cited

U.S. PATENT DOCUMENTS

| | | | |
|---|---|---|---|
| Re. 32,073 | 1/1986 | Randklev | 523/117 |
| 4,503,169 | 3/1985 | Randklev | 523/117 |
| 4,514,174 | 4/1985 | Dougherty et al. | 433/226 |
| 4,631,030 | 12/1986 | von Weissenfluh | 433/149 |
| 4,645,455 | 2/1987 | Kosmos | 433/203.1 |
| 4,657,959 | 4/1987 | Bryan et al. | 524/266 |
| 4,666,405 | 5/1987 | Ericson | 433/228.1 |
| 4,685,969 | 8/1987 | Schmid et al. | 433/228.1 |
| 4,696,646 | 9/1987 | Maitland | 433/149 |
| 4,726,770 | 2/1988 | Kurer | 433/215 |

FOREIGN PATENT DOCUMENTS 0286558 10/1988 European Pat. Off. ............ 433/226
1544776 4/1979 United Kingdom .

*Primary Examiner*—John J. Wilson
*Assistant Examiner*—Adriene B. Lepiane
*Attorney, Agent, or Firm*—Donald M. Sell; Walter N. Kirn; David R. Cleveland

[57] ABSTRACT

Photocurable restorative materials for making dental restorations usually are highly filled with fillers such as amorphous silica, quartz or glass powder having limited translucency to curing radiation. Thus the underside of the restoration may not become adequately photocured. Better curing at the underside is achieved by applying a coating of fluorescent or reflective material beneath the restorative material. When exposing the restorative material to radiant curing energy, the resulting fluorescence or reflectance by the coating enhances the degree of cure of the underside of the restoration.

22 Claims, 1 Drawing Sheet

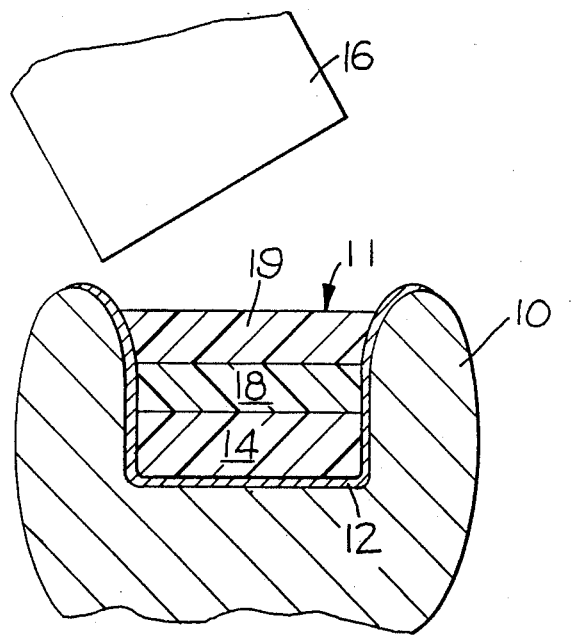

METHOD OF ENHANCING THE CURING OF A PHOTOCURABLE DENTAL RESTORATIVE MATERIAL

BACKGROUND OF THE INVENTION

1. Field of the Invention

The invention is concerned with curing photocurable restorative materials such as those used for making dental restorations. The invention also has nondental uses such as the restoration of art objects.

2. Description of the Related Art

Many dental restorative materials are cured by exposure to radiant energy, typically blue light having a wavelength of about 400 to 500 nm. Most such dental restorative materials contain an acrylate or methacrylate binder resin, a filler such as quartz powder or a finely-divided glass (e.g., radiopaque glass), and a photoinitiator. Representative dental restorative materials are described in U.S. Pat. No. 4,503,169 (Randklev), U.S. Pat. No. Re. 32,073 (Randklev), and U.K. Pat. Specification No. 1,544,776.

Because the filler affords limited translucency, photocurable dental restorative materials are desirably laid up in thin layers, typically each having a thickness from about 2 to 3 mm. The layers are successively cured by exposure to radiant energy. Even at a thickness of only 2 mm, the undersurface of the restorative material does not become as well cured as the top surface and central portions, although the difference in the degree of curing may not be great. At a thickness of 3 mm or more, the difference in degree of curing between the top and undersurfaces becomes more significant, and there is a danger that the underside of the restoration might be so undercured as to become a source of microleakage, leading to subsequent caries in adjacent healthy tooth structure. Nevertheless, there is a temptation to make each layer as thick as possible in order to save time and effort, in spite of the hazard of undercuring.

Because teeth fluoresce naturally, dental restorative materials and dental porcelains sometimes contain tiny amounts of fluorescent material to afford a life-like quality. For example, in U.S. Pat. No. 4,514,174 (Dougherty et al.), fluorescent material represents 0.0095% of the restorative of Example 1 and 0.01% of that of Example 2. In U.S. Pat. No. 4,645,455, fluorescent materials are added to porcelains in amounts as high as 6 weight percent.

SUMMARY OF THE INVENTION

The present invention permits the curing of a layer of photocurable restorative material having greater thickness than was previously feasible, while reducing undesirable differences in the degree of curing of the top and undersurfaces. This is achieved by the sequential steps of:

(a) applying to a dental substrate or model thereof a coating comprising an amount, sufficient to increase the hardness of the underside of a photocurable dental restorative after photocuring, of a (i) fluorescent material that, when exposed to radiant energy, fluoresces at a wavelength at which the restorative material photocures, or (ii) reflective material that reflects radiant energy at a wavelength at which the restorative material photocures, (b) applying a thin layer of the restorative material over the coating, and (c) exposing the layer to radiant energy of said wavelength to photocure the restorative material.

Use of a fluorescent material rather than a reflective material is ordinarily preferred. Also, because the most widely-used photocurable restorative materials are usually cured by radiant energy within the range of 400 to 500 nm, it is preferred both to apply in step (c) radiant energy within such range of wavelengths and to employ in step (a) a fluorescent material that, when exposed to such radiant energy or to energy of a longer wavelength (e.g., about 500 nm or more), fluoresces somewhere within the range of wavelengths between 400 and 500 nm.

Both the incident energy and the fluorescing or reflected energy typically will exhibit a range or band of wavelengths. Accordingly, unless otherwise indicated, references herein to particular numeric wavelengths will refer to peak wavelengths.

Even though restorative materials now being used to make dental restorations tend to be poorly translucent to radiant energy because of their filler content, some radiant energy is transmitted to the coating applied in step (a). The coating fluoresces in response to the radiant energy, or reflects the radiant energy, thereby subjecting the underside of the restorative material to photocuring radiant energy and increasing the degree of cure of the restorative near the coating. Hence, a portion of the restorative material adjacent to that underside becomes better cured than when a fluorescent or reflective coating is not used. Tests show that the hardnesses at the underside and top surfaces of a photocured restorative material are more nearly equal than when an identical specimen of the restorative material is photocured without the use of a coating containing fluorescent or reflective material.

BRIEF DESCRIPTION OF THE DRAWING

The single FIGURE of the drawing shows a schematic side elevation of a fragment of a model or die of a prepared tooth showing the creation of a dental restoration in the form of an inlay.

DETAILED DESCRIPTION

A variety of coatings can be used, depending in part upon convenience and the desired release characteristics or residual condition of the coating. Suitable coatings can be solvent-borne or curable materials. If curable, the coating can be chemically, thermally or photolytically curable. Preferred coatings include petroleum jelly, cocoa butter, synthetic lubricants such as tetrafluoroethylene-based or silicone-based lubricants, and commercial release agents. "TFE Lube" (tetrafluoroethylene) (3M) is a useful commercially available tetrafluoroethylene-based lubricant. "Super-Sep" from Kerr Manufacturing Company, "Kraxo 1711" from Contour Chemical Company, and "Modern Foil" release agent from Columbus Dental division of Miles Laboratory are useful commercially available release agents. Additional preferred coatings include ethylene oxide polyethers (such as the "Carbowax" series from Union Carbide) and addition-curable or condensation-curable silicones. The addition-curable vinyl polysiloxanes described in U.S. Pat. No. 4,657,959 (prepared without the addition of filler) constitute particularly desirable coatings.

Fluorescent materials for use in the invention include pigments and dyes. The pigments and dyes preferably have an emission peak at about 400 to about 600 nm.

Suitable pigments include "Lumogen" Yellow S 0790, BASF Corp. Suitable fluorescent dyes include rodamine dyes (such as "Basonyl" R 481, R 482, R 485, R 540, and R 560 dyes from BASF Corp., all having an emission peak at about 560 nanometers) and perylene dyes (such as "Lumogen" F Orange 240 from BASF Corp., having an emission peak at about 540 nanometers and an excitation peak at about 480 nanometers, and "Lumogen" F Red 300 from BASF Corp., having an emission peak at about 610 nanometers and an excitation peak at about 560 nanometers). Other suitable fluorescent dyes include "Lumogen" F Yellow 083 from BASF Corp., having an emission peak at about 500 nanometers and an excitation peak at about 460 nanometers, and "Lumogen" F Violet 570 from BASF Corp., having an emission peak at about 440 nanometers and an excitation peak at about 390 nanometers. Mixtures of fluorescent pigments and./or fluorescent dyes can be used if desired.

Suitable reflective materials preferably are finely-divided metallic powders. Finely-divided silver and aluminum are preferred reflective powders. Care should be taken to discourage excessive oxidation of the powder before it is mixed into the coating, so that a shiny coating can be formed. A useful aluminum-containing coating is available in a convenient form as Aluminum "Sprayon" industrial refinishing spray enamel No. 01760 from Sherwin Williams Co.

If desired, fluorescent pigments or dyes can be combined with reflective materials, although preferably the fluorescent pigments and dyes are used in the absence of fillers that would opacify the coating of fluorescent material and thus undesirably reduce the transmission of incident light.

The amount of fluorescent material or reflecting material should be sufficient to provide a reduction in the degree of cure difference between the top and underside of a cured restorative. In general, amounts of fluorescent material greater than those conventionally used for conventional photocurable dental restorative materials are employed, with amounts of about 0.01% by weight or more of fluorescent material being recommended. Reflective materials should generally be used in somewhat larger minimum quantities, e.g., at least about 1% by weight. The upper limit for the fluorescent material or reflective material is governed primarily by considerations of solubility (or suspendability if the fluorescent material or reflective material is insoluble in the coating) and economy. A preferred amount of fluorescent material is about 0.02 to about 1 weight percent, with the most preferred amount being about 0.03 to about 0.1 weight percent. A preferred amount of reflective material is about 2 to about 10 weight percent, with the most preferred amount being about 3 to about 7 weight percent.

For intraoral dental restorations, the fluorescent or reflective material can be incorporated into a coating that preferably is otherwise substantially transparent to the radiant energy applied in step (c). The coating preferably also serves as an adhesive or an adhesion-promoting primer layer that is applied to a prepared tooth before applying restorative material. For esthetic reasons, care may need to be taken to employ the fluorescent or reflective material only in areas that cannot be seen by a normal observer when the restoration is completed.

For extraoral dental restorations (e.g., custom-made inlays), the fluorescent or reflective material can be mixed with a release material that preferably is otherwise substantially transparent to the radiant energy applied in step (c). The release layer aids in removal of the restoration from the tooth model on which the restoration is prepared. Residual release material can then be cleaned off the photocured restoration after it has been removed from the model. By mixing the fluorescent or reflective material with the release agent, it is easy to ascertain visually whether the release agent and the fluorescent or reflective material have been completely cleaned off the cured restoration.

To create dental restorations of substantial thickness, it may be necessary to employ sequentially-applied layers of photocurable restorative material. In doing so, it typically will be impractical to apply inter-layer coatings of a fluorescent or reflective material. Hence, only the undersurface of a multi-layer restoration may receive a significant benefit from the fluorescent or reflective material. However, improved cure at the undersurface can provide improved assurance against microleakage. Moreover, when a multi-layer extraoral dental restoration has a better cure at its undersurface, it may be more resistant to damage when handled and placed on a tooth model or a tooth.

In the drawing, the surface of a model tooth 10 which has been prepared to receive an inlay 11, has a thin, substantially transparent coating 12 of a mixture of fluorescent material and release agent. The coating 12 covers the entire area to be contacted by the inlay and can extend slightly beyond that area. Over the coating 12 is applied a first thin layer 14 of photocurable restorative material which then is cured by exposure to light emitted from a light guide 16 of a curing lamp (not shown). Light from the lamp causes the fluorescent material in the coating 12 to luminesce, thus helping to cure the undersurface of the first layer 14. Subsequently, a second layer 18 and a third layer 19 of the restorative material are applied over the first layer 14 and sequentially cured by light from the lamp. When the second layer 18 and third layer 19 are irradiated, the fluorescent material in the coating 12 may have its primary effect upon the curing of the second and third layers at their perimeters. After the second layer and third layers have been cured, the resulting integral restoration can be removed and given a trial fitting in the patient's mouth. Before doing so, the coating 12 preferably is cleaned off the undersurface of the restoration. After a satisfactory fit has been confirmed, the restoration can be cemented into the patient's mouth using a conventional dental luting cement.

Testing

In the examples which follow, cylindrical mold cavities in a polytetrafluoroethylene mold were coated with a release agent or a mixture of the release agent and a fluorescent or reflective material. The mold cavities were each 8 mm in diameter and either 2 mm or 3 mm in height. Next a restorative material to be tested was packed into the coated cavities and covered with a thin film of transparent polyethylene. Each sample of the restorative material was cured by exposure for 20 seconds to blue light, primarily in the 420–500 nm band with a peak at 460 nm, from a "Visilux 2" visible light curing unit (3M). The end of the curing unit lightguide was held close to but not touching the restorative material. The upper and lower surfaces of each of the cured disks was then tested for hardness using a "Barber-Coleman" hardness tester equipped with identer no. GYZJ 934-1.

In the examples, unless otherwise indicated, all parts and percentages are by weight.

EXAMPLE 1

The method of the invention was carried out using three representative dental restorative materials:

Dental Restorative Material A: "Silux" restorative (3M).

Dental Restorative Material B: "P-30" restorative (3M).

Dental Restorative Material C: "Brilliant D.I." restorative (Coltene).

Each of these restorative materials was tested at two thicknesses as reported in Table A which compares the performance of identical disk pairs. One disk of each pair was cured while resting on a substantially transparent release layer containing no fluorescent or reflective material. The "Barcol A" hardness for the top surface ("Top") and the underside ("Bottom") of the resulting cured restorative disks are reported in Table A under the heading "w/o flr. material". The substantially transparent release layer was made by curing in situ at room temperature a mixture of 100 parts polymerizable vinylsiloxane, 1.5 parts siloxane crosslinker and 0.25 parts catalyst, each of which was prepared as described in Example 1 of U.S. Pat. No. 4,657,959. The other disk of each pair was cured while resting on a release layer which was identical to the layer described above except including 0.2 part "Lumogen" Yellow S 0790 fluorescent material. The Barcol A top and bottom hardnesses of the resulting cured restorative disks are reported in Table A under the heading "with flr. material".

TABLE A

| Dental Restorative Material | Thickness (mm) | Hardness, Barcol A | | | |
|---|---|---|---|---|---|
| | | w/o flr. material | | with flr. material | |
| | | Top | Bottom | Top | Bottom |
| A | 2 | 72 | 68 | 73 | 70 |
| B | " | 80 | 76 | 80 | 80 |
| C | " | 81 | 74 | 80 | 78 |
| A | 3 | 72 | 48 | 70 | 60 |
| B | " | 80 | 56 | 78 | 62 |
| C | " | 83 | 56 | 81 | 60 |

The results reported in Table A show that there are substantially smaller differences in top and bottom hardness when a coating containing fluorescent material is present during cure. The difference is especially noticeable when curing 3 mm thick disks.

EXAMPLE 2

A dental molar model of cured epoxy resin was prepared by excavating a recess for an inlay on the occlusal surface of the model. A substantially transparent release layer containing fluorescent material as described in EXAMPLE 1 was coated over the prepared recess and cured using a 20 second exposure from the light curing unit. The recess was filled to a thickness of about 3 mm with Dental Restorative Material A from EXAMPLE 1. Then the restorative material was irradiated with blue light from the curing light unit for 20 seconds to cure the restorative material fully and provide a dental restoration in the form of an inlay. Because of the uneven surfaces of the inlay, reliable hardness values could not be obtained. However, upon scratching the inlay with a sharp probe, its top and bottom surfaces appeared to be of substantially equal hardness and hence substantially equally well cured.

EXAMPLE 3

0.3 Parts of the fluorescent material used in EXAMPLE 1 were stirred into 100 parts of a commercial dental adhesive ("Scotchbond" Dual Cure dental adhesive, 3M). A thin coating of the resulting mixture was brushed onto a shallow excavation that had been prepared in a bovine tooth. The resulting coating was air-dried to a thickness of less than 1 mm. Over the dried coating was applied Dental Restorative Material A to a thickness of about 3 mm, and this was cured as in EXAMPLE 2 to provide a dental restoration that could not be removed without breaking the tooth. The restorative material appeared to be cured completely throughout its full thickness.

EXAMPLE 4

A thin coating of aluminum paint (No. 01760 "Sprayon" Enamel, Sherwin-Williams Co.) was applied to the 3 mm thick mold used in EXAMPLE 1. Dental Restorative Material A was placed in the mold and cured as in EXAMPLE 1. The cured restorative had a top hardness of 70 and a bottom hardness of 65, thus demonstrating an improvement over the use of a control coating made without reflective material (top hardness of 72, bottom hardness of 48).

When 10 percent finely-divided aluminum dust (No. A559, Fisher Scientific Co.) was added to the release coating used in EXAMPLE 1, no restorative hardness improvement over the control coating was observed. However, the aluminum-containing release coating was grey in appearance, and less shiny than the aluminum paint described above.

Various modifications and alterations of this invention will be apparent to those skilled in the art without departing from the scope and spirit of this invention and the latter should not be restricted to that set forth herein for illustrative purposes.

I claim:

1. Method of enhancing the cure of a photocurable restorative material comprising the steps of:
   (a) applying to a dental substrate or model thereof a coating comprising an amount, sufficient to increase the hardness of the underside of a photocurable dental restorative after photocuring, of a fluorescent material that, when exposed to radiant energy, fluoresces at a wavelength at which the restorative material photocures,
   (b) applying a thin layer of the restorative material over the coating, and
   (c) exposing the layer to radiant energy of said wavelength to photocure the restorative material.

2. Method as defined in claim 1, wherein the coating applied in step a) includes a release material to permit the cured restorative material to be removed from said substrate or model.

3. Method as defined in claim 1, wherein the coating applied in step (a) is substantially transparent and has a thickness less than about 1 mm.

4. Method as defined in claim 1, wherein the fluorescent material has an emission peak at about 400 to about 600 nanometers.

5. Method as defined in claim 1, wherein the fluorescent material comprises a pigment.

6. Method as defined in claim 5, wherein the pigment is yellow.

7. Method as defined in claim 1, wherein the fluorescent material comprises a rodamine or perylene dye.

8. Method as defined in claim 1, wherein the amount of fluorescent material is at least about 0.01 weight percent of the coating.

9. Method as defined in claim 1, wherein the amount of fluorescent material is about 0.02 to about 1 weight percent of the coating.

10. Method as defined in claim 1, wherein the coating is substantially free from opacifying filler.

11. Method as defined in claim 1, wherein the thickness of the layer applied in step (b) exceeds 2 mm.

12. Method as defined in claim 1, wherein after the restorative material is photocured, it comprises an occlusal inlay.

13. Method as defined in claim 1, wherein the substrate comprises a tooth or teeth.

14. Method of enhancing the cure of a photocurable restorative material comprising the steps of:

(a) applying to a dental substrate or model thereof a coating comprising an amount, sufficient to increase the hardness of the underside of a photocurable dental restorative after photocuring, of a reflective material that reflects radiant energy at a wavelength at which the restorative material photocures, (b) applying a thin layer of the restorative material over the coating, and (c) exposing the layer to radiant energy of said wavelength to photocure the restorative material.

15. Method as defined in claim 14, wherein the reflective material comprises finely-divided aluminum powder.

16. Method as defined in claim 14, wherein the amount of reflective material is at least about 1 weight percent of the coating.

17. Method as defined in claim 14, wherein the coating applied in step (a) includes a release material to permit the cured restorative material to be removed from said substrate or model.

18. Method as defined in claim 14, wherein the coating applied in step (a) is substantially transparent and has a thickness less than about 1 mm.

19. Method as defined in claim 14, wherein the coating is substantially free from opacifying filler.

20. Method as defined in claim 14, wherein the thickness of the layer applied in step (b) exceeds 2 mm.

21. Method as defined in claim 14, wherein after the restorative material is photocured, it comprises an occlusal inlay.

22. Method as defined in claim 14, wherein the substrate comprises a tooth or teeth.

* * * * *